US00PP13306P2

(12) United States Plant Patent
Klemm

(10) Patent No.: US PP13,306 P2
(45) Date of Patent: Dec. 3, 2002

(54) GERANIUM PLANT NAMED 'KLEFLASAL'

(75) Inventor: Nils Klemm, Stuttgart (DE)

(73) Assignee: Klemm & Sohn GmbH + Co. KG, Stuttgart (DE)

( * ) Notice: Subject to any disclaimer, the term of this patent is extended or adjusted under 35 U.S.C. 154(b) by 0 days.

(21) Appl. No.: 09/876,935

(22) Filed: Jun. 11, 2001

(51) Int. Cl.[7] ..... A01H 5/00

(52) U.S. Cl. ..... Plt./328

(58) Field of Search ..... Plt./328, 325, 327

*Primary Examiner*—Bruce R. Campell
*Assistant Examiner*—June Hwu
(74) *Attorney, Agent, or Firm*—C. A. Whealy

(57) ABSTRACT

A new and distinct cultivar of Geranium plant named 'Kleflasal', characterized by its upright and rounded growth habit; freely basal branching habit; star-shaped green-colored leaves with darker green zonation pattern; and star-shaped pink-colored single flowers.

1 Drawing Sheet

BOTANICAL CLASSIFICATION/CULTIVAR DESIGNATION

*Pelagaronium×hortorum* cultivar Kleflasal.

BACKGROUND OF THE INVENTION

The present invention relates to a new and distinct cultivar of Geranium plant, botanically known as *Pelargonium×hortorum*, and hereinafter referred to by the name 'Kleflasal'.

The new Geranium is a product of a planned breeding program conducted by the Inventor in Stuttgart, Germany. The objective of the breeding program was to develop new Geraniums with unique flower forms, freely-branching growth habit and interesting flower and foliage colors.

The new Geranium originated from a cross made by the Inventor in July, 1996 of the *Pelargonium×hortorum* cultivar Gemini, disclosed in U.S. Plant Pat. No. 5,980, as the female, or seed, parent with an unidentified proprietary selection of *Pelargonium×hortorum*, not patented, as the male, or pollen, parent. The cultivar Kleflasal was discovered and selected by the Inventor as a flowering plant within the progeny from this cross in a controlled environment in Stuttgart, Germany, in June, 1997.

Asexual reproduction of the new cultivar by terminal cuttings taken at Stuttgart, Germany, since July, 1997 has shown that the unique features of this new Geranium are stable and reproduced true to type in successive generations of asexual reproduction.

SUMMARY OF THE INVENTION

The following traits have been repeatedly observed and are determined to be the unique characteristics of 'Kleflasal'. These characteristics in combination distinguish 'Kleflasal' as a new cultivar and distinguish it from other known Geranium cultivars:

1. Upright and rounded growth habit.
2. Freely basal branching habit.
3. Star-shaped green-colored leaves with darker green zonation pattern.
4. Star-shaped pink-colored single flowers.

Plants of the new Geranium differ primarily from plants of the cultivar Gemini in flower color. In addition, in side-by-side comparisons conducted in Stuttgart, Germany, plants of the new Geranium are stronger and more vigorous than plants of the cultivar Gemini. Plants of the new Geranium differ primarily from plants of the male selection in leaf and petal shape.

BRIEF DESCRIPTION OF THE PHOTOGRAPH

The accompanying colored photograph illustrates the overall appearance of the new cultivar, showing the colors as true as it is reasonably possible to obtain in colored reproductions of this type. The photograph comprises a side perspective view of a typical flowering plant of 'Kleflasal' that was grown for about three months in a 12-cm container. Flower and foliage colors in the photograph may differ slightly from the color values cited in the detailed botanical description which accurately describe the colors of the new Geranium.

DETAILED BOTANICAL DESCRIPTION

The cultivar Kleflasal has not been observed under all possible environmental conditions. The phenotype may vary somewhat with variations in environment such as temperature and light intensity, without, however, any variance in genotype. The following observations, measurements and comparisons describe plants that were planted in January in 12-cm pots in Stuttgart, Germany, and grown for about three months under commercial practice in a glass-covered greenhouse with day temperatures about 18 to 22° C., night temperatures about 15 to 18° C. and light levels about 20,000 to 50,000 lux. In the following description, color references are made to The Royal Horticultural Society Colour Chart except where general terms of ordinary dictionary significance are used.

Botanical classification: *Pelargonium×hortorum* cultivar Kleflasal.

Parentage:

*Female parent.*—*Pelargonium×hortorum* cultivar Gemini, disclosed in U.S. Plant Pat. No. 5,980.

*Male parent.*—Unidentified proprietary selection of *Pelargonium×hortorum*, not patented.

Propagation:

*Type cutting.*—Terminal cuttings.

*Time to initiate roots.*—Summer: About 8 days at 22° C. Winter: About 11 days at 20° C.

*Time to develop roots.*—Summer: About 19 days at 22° C. Winter: About 22 days at 20° C.

*Root description.*—Fibrous, freely branching and white in color.

Plant description:

*General appearance.*—Upright and rounded growth habit; densely foliated. Appropriate for 12-cm containers.

*Crop time.*—About three months are required to produced a finished flowering plant in 12-cm container.

*Growth and branching habit.*—Vigorous and freely basal branching; about six lateral branches develop towards the plant base. Pinching, that is, removal of terminal apices, is typically not required.

*Plant height* (*to top of flower umbels*).—About 30 cm.

*Plant height* (*to top of foliar plane*).—About 18 cm.

*Plant width.*—About 20 cm.

*Lateral branches.*—Length: About 10 cm. Internode length: About 1 to 1.5 cm. Texture: Slightly pubescent. Color: 139D.

*Foliage description.*—Leaves simple, generally symmetrical, alternate arrangement. Quantity of leaves per lateral branch: About 6 to 8. Length, mature leaves: About 4 cm. Width, mature leaves: About 6 cm. Shape: Star-shaped. Apex: Rounded. Base: Obtuse. Margin: Entire. Venation pattern: Palmate. Texture, both surfaces: Slightly pubescent, rough. Color: Young and mature foliage, upper surface: 137B; zonation pattern, 200B in color, located about 1 to 5 mm from the margin, and about 1 to 1.5 cm in width. Young and mature foliage, lower surface: 137C. Venation, upper surface: 137C. Venation, lower surface: 138B. Petiole: Length: About 5 cm. Diameter: About 2 mm. Texture, both surfaces: Slightly pubescent. Color, both surfaces: 139D.

Flower description:

*Flower arrangement and type.*—Pink-colored flowers arranged in spherical umbels arising from apical leaf axils. Umbels displayed above the foliage. Freely flowering; at full flowering about 6 to 9 open umbels and about 3 to 5 developing umbels per plant. Flowers single in form, flat and star-shaped. Flowers last about 8 to 14 days on the plant. Umbels persistent, flowers not persistent. Flowers not fragrant.

*Flowering season.*—Year-round under greenhouse conditions. In the garden, flowering is continuous from spring until fall.

*Umbels.*—Height: About 5 to 8 cm. Diameter: About 7 to 10 cm. Number of flowers and flower buds per umbel: About 14 to 25. Flower diameter: About 3.75 cm. Flower depth (height): About 9 mm.

*Flower buds.*—Length: About 9 mm. Diameter: About 3.5 mm. Shape: Elliptic. Color: 146A.

*Petals.*—Quantity: Five per flower arranged in a single whorl. Length: About 2 cm. Width: About 1.5 cm. Shape: Roughly diamond-shaped. Apex: Praemorse. Base: Attenuate to acute. Margin: Entire below the apex. Texture, both surfaces: Smooth. Color: When opening, upper surface: 49A. When opening, lower surface: 49C. Fully opened, upper surface: 49A; towards base, 49D; with subsequent development, 36A. Fully opened, lower surface: 49D. Venation, upper surface: 50B. Venation, lower surface: 49C.

*Sepals.*—Quantity: Five, arranged in a single whorl. Length: About 7 mm. Width: About 2 mm. Shape: Elliptic. Apex: Narrowly acute. Margin: Entire. Texture, both surfaces: Pubescent, velvety. Color, upper and lower surfaces: 139C.

*Peduncle* (*umbel stem*).—Length: About 15 to 28 cm. Diameter: About 2 to 5 mm. Angle: Erect. Strength: Moderately strong. Texture: Slightly pubescent. Color: 139D.

*Pedicel* (*individual flower stem*).—Length: About 3 cm. Diameter: About 1.5 mm. Angle: Erect. Strength: Moderately strong. Texture: Slightly pubescent. Color: 177A.

*Reproductive organs.*—Androecium: Anther quantity: Five per flower. Anther length: About 3 mm. Anther shape: Ovate. Anther color: 33C. Pollen amount: Moderate. Pollen color: 33C. Gynoecium: Pistil quantity: One per flower. Pistil length: About 4 to 8 mm. Stigma shape: Five-parted, star-shaped. Stigma color: 57C. Style length: About 3.5 mm. Style color: 57C. Ovary color: 149D.

*Seed.*—Length: About 3 to 6 mm. Diameter: About 1.5 to 2 mm. Shape: Ovoid. Color: Brownish.

Disease resistance: Resistance to pathogens common to Pelargonium has not been observed on plants grown under commercial production conditions.

It is claimed:

1. A new and distinct cultivar of Geranium plant named 'Kleflasal', as herein illustrated and described.

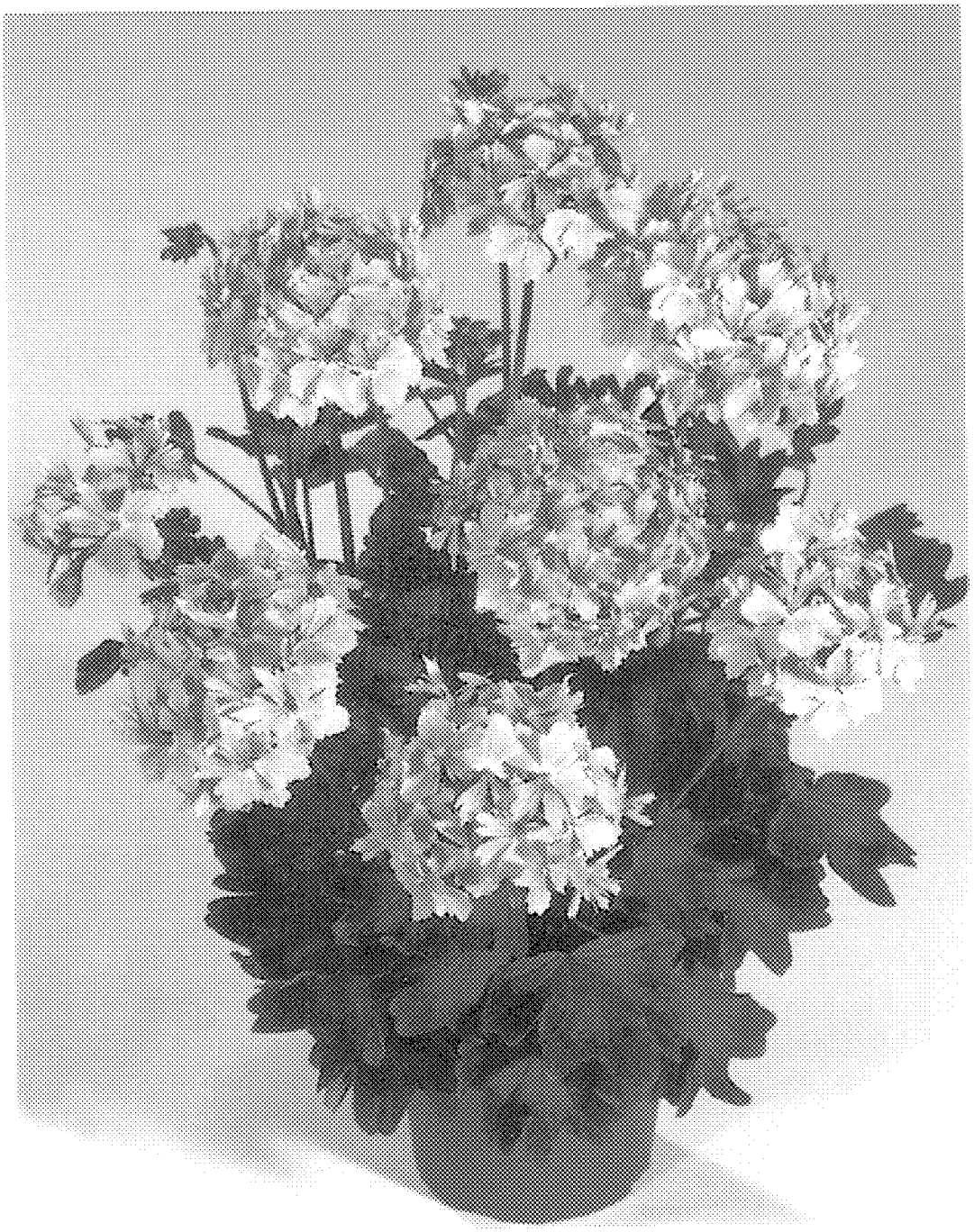

* * * * *